US00RE34165E

United States Patent [19]

Goldstein et al.

[11] E Patent Number: Re. 34,165

[45] Reissued Date of Patent: Jan. 19, 1993

[54] POTENT THYMOPENTIN ANALOGS

[75] Inventors: Gideon Goldstein, Short Hills; George Heavner, Flemington; Daniel Kroon; Tapan Audhya, both of Bridgewater, all of N.J.

[73] Assignee: Ortho Pharmaceutical Corporation, Raritan, N.J.

[21] Appl. No.: 514,184

[22] Filed: Apr. 25, 1990

Related U.S. Patent Documents

Reissue of:

[64] Patent No.: 4,629,723
Issued: Dec. 16, 1986
Appl. No.: 625,344
Filed: Jun. 27, 1984

[51] Int. Cl.[5] ..... A61K 37/02; A61K 37/43; C07K 7/06; C07K 7/48

[52] U.S. Cl. ..... 514/17; 530/330

[58] Field of Search ..... 514/17; 530/330, 301

[56] References Cited

U.S. PATENT DOCUMENTS

| | | | |
|---|---|---|---|
| 4,002,740 | 1/1977 | Goldstein et al. | 514/14 |
| 4,077,949 | 3/1978 | Goldstein | 530/301 |
| 4,190,646 | 2/1980 | Goldstein et al. | 514/17 |
| 4,261,886 | 4/1981 | Goldstein et al. | 530/330 |
| 4,305,852 | 12/1981 | Garsky | 530/330 |
| 4,309,340 | 1/1982 | Sarantakis | 530/330 |
| 4,361,673 | 11/1982 | McGregor | 530/330 |
| 4,420,424 | 12/1983 | Geiger et al. | 530/330 |
| 4,505,853 | 3/1985 | Goldstein et al. | 530/301 |

FOREIGN PATENT DOCUMENTS

| | | |
|---|---|---|
| 62550 | 4/1981 | Australia . |
| 43423 | 12/1985 | Australia . |
| 1269498 | 5/1990 | Canada . |
| 0018182 | 10/1980 | European Pat. Off. . |
| 0025897 | 4/1981 | European Pat. Off. . |
| 0037246 | 10/1981 | European Pat. Off. . |
| 146266 | 6/1985 | European Pat. Off. . |
| 164654 | 12/1985 | European Pat. Off. . |
| 2938420 | 4/1981 | Fed. Rep. of Germany . |
| 61098 | 9/1984 | Israel . |

OTHER PUBLICATIONS

Audhya et al, "Contrasting biological activities of thymopoietin and splenin, two closely related . . . ", PNAS USA vol. 81, May 1984, pp. 2847–2849.

Chemical Abstract vol. 102:130052d (1985).

Schulz et al, *Principles of Protein Structure*, Springer-Verlag, 1979, pp. 14–16.

Dayhoff, *Atlas of Protein Sequence and Structure*, vol. 5, National Biomedical Res. Found. 1972, pp. 89–96, 99.

*Selected Methods In Cellular Immunology*, Mishell et al, eds. W. H. Freeman and Co. 1980, pp. 30–37.

Audhya et al, Int. J. Peptide Protein Res., 22:568–72 (1983).

Aiuti et al, Lancet, 1:551–555 (1983).

Levinsky et al, "Primary Infectious Diseases", Wedgewood, Rosen and Paul, eds., 19:273–76 (1983).

M. E. Weksler et al, J. Exp. Med., 148:996–1006 (1978).

Audhya, Biochem., 20:6195–6200 (1981).

Audhya et al, Int. J. Peptide Protein Res., 22:187–193 (1983).

Tischio et al, Int. J. Peptide Protein Res., 14:479–484 (1979).

Chipens et al, Latv PSR Zinat. Akad. Vestis. Kim. Ser., 6:752–753 (1984).

*Primary Examiner*—Jeffrey E. Russel
*Attorney, Agent, or Firm*—Howson and Howson

[57] ABSTRACT

Immunoregulating peptides are disclosed which are more potent than thymopentin or splenin and are useful for their effects on the immune system, especially the treatment of thymic deficiencies.

14 Claims, 1 Drawing Sheet

LEGEND
- TP-5
- AC-ARG-PRO-ASP-VAL-PHE
- FORMYL-ARG-PRO-ASP-VAL-PHE
- ASP-ARG-TYR-LYS-VAL

LEGEND

- TP-5
- AC-ARG-PRO-ASP-VAL-PHE
- FORMYL-ARG-PRO-ASP-VAL-PHE
- ASP-ARG-TYR-LYS-VAL

POTENT THYMOPENTIN ANALOGS

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates generally to new immunomodulatory peptides and particularly to analogs of the peptide thymopentin which have greatly increased potency.

2. Description of the Art

U.S. Pat. Nos. 4,190,646 and 4,261,886 disclose various pentapeptides having activity similar to the long chain polypeptide known as thymopoietin, which is described in U.S. Pat. Nos. 4,002,740 and 4,077,949. Thymopoietin selectively stimulates the differentiation of T cells. The pentapeptide disclosed in the U.S. Pat. No. 4,190,646 which has the sequence H-ARG-LYS-ASP-VAL-THY-OH, is known as the thymopoietin pentapeptide or "thymopentin". The biological activity of certain of these peptides is described in an article by M. E. Weksler, et al., J. Exp. Med. 148: 996-1006 (1978). The above U.S. patents and article are incorporated herein by reference. U.S. Pat. Nos. 4,361,673 and 4,420,424 also disclose various peptides asserted to have activity similar to thymopoietin. A peptide of similar structure isolated from bovine spleen and termed "splenin" is described in Audhya, et al., Biochemistry, 20, 6195-6200 (1981) and Proc. Nat. Acad. Sci. (USA), 81, 2847-2849 (May 1984). This material stimulates induction of both T cells and B cells.

Certain enzyme-resistant immunomodulatory peptides are disclosed in our copending application Ser. No. 553,281, filed Nov. 18, 1983, which is incorporated herein by reference.

Thymopentin has been shown to exert a modulatory effect on the immune system of animals and humans and is thus useful for treatment of diseases involving defects in immune function, whether such defects are manifested as deficiencies or excesses of immune function. See for example Audhya, T. and Goldstein, G., Int. J. Pept. Protein Res., 22, 568-572 (1983); Aiuti, et al., Lancet 1:551-555 (1983); and Levinsky, et al., in "Primary Immunodeficiency Diseases", Wedgewood, Rosen, and Paul, eds, 19, 273-276 (1983). Reference is made to these articles and to the above-described patents and article for a discussion of other background material and the biological processes involved in the present invention.

The present invention provides peptides and peptide compositions which are surprisingly more potent than thymopentin or splenin and thus offer significant advantages in the treatment of immune defects.

SUMMARY OF THE INVENTION

The present invention relates to novel peptides having the following formula:

$$R-V-W-X-Y-Z-R^1 \quad (I)$$

or a pharmaceutically-acceptable acid- or base-addition salt thereof, wherein:

R is H, loweralkyl, formyl, or loweralkanoyl;

V is ARG or D-ARG;

W is LYS, D-LYS, PRO, dehydro PRO, or AIB;

X is ASP, D-ASP, GLU or D-GLU;

Y is VAL, LYS, LEU, ILE, GLU, ALA, GLN, D-VAL, D-LYS, D-LEU, D-ILE, D-GLU, D-ALA, and D-GLN;

Z is PHE, HIS, TRP, D-PHE, D-HIS, or D-TRP;

$R^1$ is OH or $NR^2R^3$; and $R^2$ and $R^3$ are each independently selected from H and loweralkyl;

provided that when W is LYS, X is D-ASP, GLUE, or D-GLU, and Y is VAL, Z is other than PHE.

It has been surprisingly found that the subject peptides possess thymopentin-like or splenin-like activity at a potency approximately ten times that of thymopentin or splenin itself.

The subject peptides wherein W is PRO, dehydro PRO, or AIB also possess surprising resistance to degradation by enzymes, as disclosed in the above referenced patent application.

DETAILED DESCRIPTION OF THE INVENTION

Figure 1:
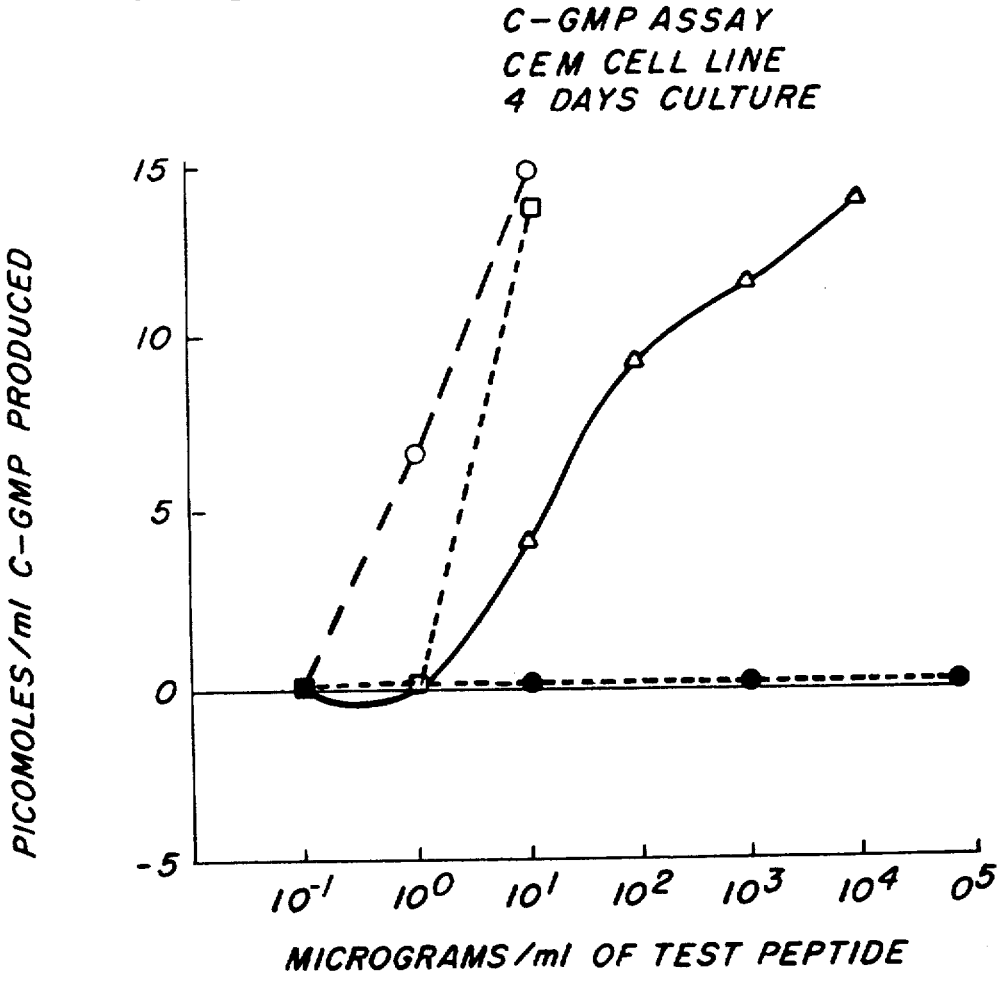

As indicated above, this invention is concerned with new peptides having thymopoietin-like activity, therapeutic compositions containing these peptides, and methods for use thereof.

In its broadest scope, the present invention provides peptides having the following formula:

$$R-V-W-X-Y-Z-R^1 \quad (I)$$

or a pharmaceutically acceptable acid- or base-addition salt thereof, wherein R, V, W, X, Y, Z, and $R^1$ are as defined above. Preferred peptides of the present invention are those of Formula (I) wherein Z is PHE, D-PHE, HIS, or D-HIS, and particularly wherein W is also PRO. More preferred peptides are those of Formula I wherein R is hydrogen, or loweralkanoyl, V is ARG, X is ASP, and Z is PHE or HIS, and more particularly wherein W is also PRO. Still more preferred peptides are H-ARG-LYS-ASP-VAL-PHE-OH, H-ARG-LYS-ASP-VAL-HIS-OH, H-ARG-PRO-ASP-VAL-PHE-OH, H-ARG-PRO-ASP-VAL-HIS-OH, H-ARG-LYS-ASP-VAL-TRP-OH, α-acetyl-ARG-PRO-ASP-VAL-PHE-$NH_2$, and loweralkanoyl-ARG-PRO-ASP-VAL-PHE-OH.

As used herein, the term "loweralkyl" includes branched and straight-chain saturated hydrocarbons having from one to six carbon atoms, such as methyl, ethyl, propyl, isopropyl, pentyl, hexyl, and the like, while the term "loweralkanoyl" means loweralkyl $$\overset{O}{\overset{\|}{C}}-.$$

As acids which are able to form salts with these peptides there may be mentioned inorganic acids such as hydrochloric acid, hydrobromic acid, perchloric acid, nitric acid, thiocyanic acid, sulfuric acid, phosphoric acid, and the like, and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalenesulfonic acid, sulfanilic acid, or the like.

As bases which are able to form salts with these peptides, there may be mentioned inorganic bases such as sodium hydroxide, ammonium hydroxide, potassium hydroxide, and the like, and organic bases such as mono-, di-, and tri-alkyl and aryl amines (e.g., triethylamine, diisopropylamine, methylamine, dimethylamine, and the like) and optionally substituted ethanolamines (e.g., ethanolamine, diethanolamine, and the like).

Throughout this disclosure, the amino acid components of the peptides and certain materials used in their preparation are identified by abbreviations for convenience. These abbreviations are as follows:

| Amino Acid | Abbreviation |
|---|---|
| L-alanine | ALA |
| D-alanine | D-ALA |
| L-arginine | ARG |
| D-arginine | D-ARG |
| L-aspartic acid | ASP |
| D-aspartic acid | D-ASP |
| L-glutamic acid | GLU |
| D-glutamic acid | D-GLU |
| L-glutamine | GLN |
| D-glutamine | D-GLN |
| L-histidine | HIS |
| D-histidine | D-HIS |
| L-isoleucine | ILE |
| D-isoleucine | D-ILE |
| L-leucine | LEU |
| D-leucine | D-LEU |
| L-lysine | LYS |
| D-lysine | D-LYS |
| α-methylalanine | AIB |
| L-phenylalanine | PHE |
| D-phenylalanine | D-PHE |
| L-proline | PRO |
| L-tryptophan | TRP |
| D-tryptophan | D-TRP |
| L-valine | VAL |
| D-valine | D-VAL |

The peptides of the invention may generally be prepared following known techniques. Conveniently, the peptides may be prepared following the solid-phase synthetic technique initially described by Merrifield in JACS, 85, 2149-2154 (1963). Such methods are also disclosed in certain of the prior art patents referred to above. Other techniques may be found, for example, in M. Bodanszky, et al., Peptide Synthesis, John Wiley & Sons, second edition, 1976, as well as in other reference works known to those skilled in the art. Appropriate protective groups usable in such syntheses and their abbreviations will be found in the above text, as well as in J. F. W. McOmie, Protective Groups in Organic Chemistry, Plenum Press, New York, 1973. Both of these books are incorporated herein by a reference. The common protective groups used herein are t-butyloxycarbonyl (BOC), benzyl (BZL), t-amyloxycarbonyl (AOC), tosyl (TOS), o-bromo-phenylmethoxycarbonyl (BrZ), 2-6-dichlorobenzyl ($BZLCl_2$), and phenylmethoxycarbonyl (Z or CBZ).

The peptides of this invention wherein X is ASP or D-ASP have been found to exhibit biological activity similar to thymopoietin, as disclosed in the above-referenced United States patents and articles. This biological activity is evidenced by an assay measuring induction of cyclic-GMP production in a human T-cell line in comparison with thymopoietin. The induction of c-GMP production by a test peptide in this assay indicates the ability of the test peptide to bind to the thymopoietin receptor site on the cell and induce thymopoietin-like biological activity. As can be seen from the results presented below, the subject peptides are up to about ten times more potent than thymopentin, thus offering a significant advantage. Because of the expense of preparing peptides and the rapid degradation of peptides often observed in living systems, peptides such as those herein which have increased potency are greatly prized.

The biological activity of the subject peptides wherein X is ASP or D-ASP is also indicated by the binding of these peptides to the cell membrane receptor for the active site of thymopoietin.

The peptides of this invention wherein X is GLU or D-GLU exhibit biological activity similar to splenin and cause the differentiation of both Thy-1$^-$ cells to Thy-1$^+$ T cells and Lyb-2$^-$ cells to Lyb-2$^+$ B cells as shown in the assay of Scheid, et al., J. Exp. Med. 147: 1727-1743 (1978).

Prior to the making of the present invention, it was completely unexpected that one would be able to prepare peptides having such increased potency compared to thymopentin by replacing the amino acid tyrosine in the five-position by phenyalanine, histidine, or tryptophan. The references described above generally indicate the necessity of a tyrosine or tyrosine-like amino acid residue in position five. There was certainly no suggestion in the art that one could achieve such greatly-increased potency by use of the subject peptides.

Because of the immunomodulatory characteristics of the subject peptides, they are therapeutically useful in the treatment of humans and animals, since they have the capability for inducing the differentiation of lymphopoietic stem cells in the haemopoietic tissues into thymus-derived cells (T cells) which are capable of involvement in the immune response of the body. As a result, the subject peptides are considered to have multiple therapeutic uses.

Primarily, since the compounds have the capability of carrying out certain of the indicated functions of the thymus, they have application in various thymic function and immunity areas. One such application is in the treatment of DiGeorge Syndrome, a condition in which there is congenital absence of the thymus. Administration of one of the subject peptides to a sufferer from DiGeorge Syndrome will assist in overcoming this deficiency. Those of skill in the immunological art can readily determine the appropriate route for administration (preferably parenterally) and can determine the effective amount of one of the subject peptides for treatment of DiGeorge Syndrome. Because the subject peptides are more potent than thymopentin, they are more therapeutically useful than prior art peptides.

Additionally, the subject peptides are considered useful in assisting the collective immunity of the body, in that they will increase or assist in therapeutic stimulation of cellular immunity and thereby are useful in the treatment of diseases involving chronic infection, such as fungal or mycoplasma infections, tuberculosis, leprosy, acute and chronic l and viral infections and the like.

The subject compounds are generally considered to be useful in any area in which cellular immunity is an issue and particularly where there are deficiencies in immunity such as in the DiGeorge syndrome mentioned above. Thus, where there is an excess of antibody production due to unbalanced T cells and B cells, the subject peptides can correct this condition by stimulating T cell production. Thus, they are expected to be of therapeutic use in certain autoimmune diseases in which damaging antibodies are produced, such as systemic lupus erythematosis, rheumatoid arthritis, or the like.

The subject peptides wherein X is GLU or D-GLU are also useful to induce the differentiation of precursor B cells into mature B cells capable of producing antibody. They are thus useful in treatment of such conditions as X-linked infantile hypogammaglobulinemia, where a defect in such differentiation mechanism is present.

In their broadest application, the subject compounds are useful for regulating the immune system of a subject, human or animal, in need of such regulation. As used herein, the term "regulate" means that the subject compounds cause the immune system to return from an abnormal, diseased state to a normal, balanced state. While this regulation may well find great application in the correction of immunological deficiencies (e.g., DiGeorge syndrome), it is also applicable to correct conditions of excess immunological activity (e.g., autoimmune diseases). The present invention therefore includes methods for regulating the immune system of a subject in need of such regulation which comprises administering to said subject an immunoregulatorally-effective amount of one of the subject compounds, as well as pharmaceutical compositions for practicing these methods.

The present invention provides a method for treatment of conditions resulting from relative or absolute T cell or B cell deficiencies in a subject (human or animal) having such a condition which comprises administering to the subject a therapeutically-effective amount of a peptide of formula (I). The invention also provides a method for treatment of conditions resulting from relative or absolute deficiencies of the thymus of a subject which comprises administering to said subject a therapeutically-effective amount of a peptide of formula (I). As used herein, the term "therapeutically-effective amount" means an amount which is effective to treat conditions resulting from T cell or B cell deficiencies, or deficiencies of the thymus, respectively. The invention also provides a method for inducing lymphopoietic stem cells of a subject to develop the characteristics of thymus-derived lymphocytes which comprises administering to the subject an effective inducing amount of a peptide of formula (I). The invention also provides a method for inducing precursor B cells of a subject to develop the characteristics of mature B cells which comprises administering to the subject an effective inducing amount of a peptide of formula (I). The invention further provided pharmaceutical compositions for practicing those methods.

To prepare the pharmaceutical compositions of the present invention, a peptide of formula I or a base or acid addition salt thereof is combined as the active ingredient in intimate admixture with a pharmaceutical carrier according to conventional pharmaceutical compounding techniques. This carrier may take a wide variety of forms depending on the form of preparation desired for administration, e.g., sublingual, rectal, nasal, oral, or parenteral. In preparing the compositions in oral dosage form, any of the usual pharmaceutical media may be employed, such as for example, water, oils, alcohols, flavoring agents, preservatives, coloring agents and the like in the case or oral liquid preparation (e.g., suspensions, elixirs, and solutions) or carriers such as starches, sugars, diluents, granulating agents, lubricants, binders, disintegrating agents, and the like in the case of oral solid preparations (e.g., powders, capsules, and tablets). Controlled release forms may also be used. Because of their ease in administration, tablets and capsules represent the most advantageous oral dosage unit form, in which case solid pharmaceutical carriers are obviously employed. If desired, tablets may be sugar coated or enteric coated by standard techniques.

For parenteral products, the carrier will usually comprise sterile water, although other ingredients to aid solubility or for preservation purposes (for example) may be included. Injectable suspensions may also be prepared, in which case appropriate liquid carriers, suspending agents, and the like may be employed.

The subject peptides are generally active when administered parenterally in amounts above about 1 $\mu$g/kg of body weight. For treatment of DiGeorge Syndrome, the peptides may be administered parenterally from about 0.1 to about 10 mg/kg body weight. Generally, the same range of dosage amounts may be used in treatment of the other diseases or conditions mentioned where immunodeficiency is to be treated. Larger amounts (e.g., about 10–1000 mg/kg body weight) are useful for suppressing excess immune activity.

The following examples are presented to illustrate the invention without intending specifically limiting the invention thereto. In the examples and throughout the specification, parts are by weight unless otherwise indicated.

EXAMPLE I

Arginyl-Lysyl-Aspartyl-Valyl-Phenylalanine, solvated BOC-PHE-O-$CH_2$-Resin

Chlormethylated Resin (1.04 mmoles Cl/g; 5 g) and anhydrous KF (0.44 g; 7.5 mmoles) were added to a solution of BOC-PHE-OH (1.33 g; 5 mmoles) in DMF (40 ml) in a round bottom flask equipped with an overhead stirrer. The reaction mixture was stirred at 65° C. for 24 hours. The resin was then filtered and washed extensively with DMF, DMF/$H_2O$ (1:0, $H_2O$; EtOH/-$H_2O$ (1:1), EtOH and $CH_2Cl_2$. The substitution of BOC-PHE-OH on the resin was 0.545 mmoles per g of resin based on amino acid analysis.

ARG-LYS-ASP-VAL-PHE

Z-ARG(Z,Z)-LYS(Z)-ASP( BZL)-VAL-PHE-$OCH_2$-Resin was assembled manually by solid phase method. The amino acid derivatives and DCC were used in three fold excess for the following couplings: Z-ARG(Z,Z)-OH, BOC-LYS(Z)-OH, BOC-ASP( BZL)-OH and BOC-VAL-OH. The peptide-resin (3.1 g) was then cleaved with HF/Anisol (9:1; 30 ml) for 1 h at 0° C. After removal of the HF/anisol, the peptide-resin mixture was filtered and washed with ether (3×20 ml). The peptide was extracted with 5 percent HOAc/$H_2O$ (3×50 ml) and lyophilized to give 800 mg of product. The crude peptide was then purified on a Sephadex-SPC-25 column (80 cm×2.5 cm) equilibrated with 0.2M $NH_4OAc$, pH 5. The flow rate was 85 ml/hr and fractions of 10 ml/tube were collected. The desired peptide eluted between tubes 145–167. These fractions were pooled and lyophilized to give 750 mg of material. This peptide was chromatographed further on a Sephadex G-10 Column (80 cm×2.5 cm) using $H_2O$. The flow rate was 18 ml/hr and fractions of 10 ml/tube were collected. The title peptide eluted between tubes 21–26.

Thin layer chromatography (Silica Gel F60; 200 microns). $R_f$ 0.23 (n-BuOH/HOAc/$H_2O$=4:1:1). $R_f$ 0.11 ($NH_4OH$/2-Propanol=37:84).

Amino Acid Analysis: Arg, 1.04; Lys, 1.00; Asp, 1.04; Val, 0.97 and Phe, 1.00; peptide content: 88 percent.

HPLC: Whatman Partisil-ODS-1 Column. 10 percent $CH_3OH$/0.02M $KH_2PO_4$; pH 3.5. Flow rate: 2 ml/min. Retention time: 8.10 min.

EXAMPLE II

$N^{\alpha}$-Acetyl-Arginyl-Prolyl-Aspartyl-Valyl-Phenylaline

The title peptide was synthesized by the solid phase method, starting with BOC-PHE Merrifield resin (12.03 g, 0.51 meq/g). The resin was sequentially coupled with three equivalents of BOC-VAL, BOC-$\beta$-BZL-ASP, and BOC-PRO. The coupling agent was 1:1 DCC:HOBT in 4:1 $CH_2Cl_2$:DMF throughout the synthesis.

Approximately ⅓ of this tetrapeptide resin was reserved. The remainder was coupled with $N^{g}$-TOS-$N^{\alpha}$-AOC-ARG, employing the coupling conditions as above.

Approximately ½ of the pentapeptide resin was reserved. The remainder was treated with TFA and neutralized with DIEA. This was then treated with $Ac_2O$ (3 ml) and DMAP (0.3 g) in $CH_2Cl_2$ (40 ml) for 60 min. The resin was washed, dried and cleaved in HF (40 ml): anisole (10 ml) at 0° for 60 min. The residual solids were extracted with 10 percent HOAc and lyophilized to give 1.36 crude peptide.

The crude peptide was purified on Sephadex DEAE 2.6×90 cm: 0.05M $NH_4HCO_3$, pH 5 (3.5 L), 100 ml/hr flow rate, 13 ml fractions, 206 nm detector. Fractions 170–205 were collected and lyophilized to give the title compound, 830 mg.

TLC: Silica Gel, 250$\mu$.

| Solvent | $R_f$ |
|---|---|
| 5:5:3:1 EtOAc:pyr:$H_2O$:HOAc | 0.38 |
| 4:1:5 nBuOH:HOAc:$H_2O$, upper phase | 0.41 |
| 1:1 Trifluoroethanol:$NH_4OH$ | 0.75 |

Amino Acid Analysis: Arg, 1.02; Pro, 0.98; Asp 0.97; Val, 1.02; Phe, 1.01; peptide content: 65.3 percent.

EXAMPLE III

$N^{\alpha}$-Formyl-Arginyl-Propyl-Aspartyl-Valyl-Phenylalanine

The title peptide was prepared by the solid phase method, starting with ($N^{g}$-TOS-$N^{\alpha}$-AOC)-ARG-PRO-($\beta$-BZL)-ASP-VAL-PHE resin ester from Example II (ca 2 mmol). After deprotecting with 1:1 TFA/$CH_2Cl_2$ and neutralizing with DIEA, the resin was treated with p-nitrophenyl formate (1.0 g) and HOBT (0.9 g) in 5:1 $CH_2Cl_2$:DMF (30 ml) for 16 h. The resin was washed and retreated with p-nitrophenyl formate (1.0 g) and DMAP (0.2 g) in $CH_2Cl_2$ for 1 h.

The formyl peptide resin was cleaved in HF (60 ml) and anisole (10 ml) at 0° for 1 h. The residual solids were treated with 0.2 percent $NH_4OH$ and the extract lyophilized to give 1.00 g colorless solid.

The peptide was purified on Sephadex DEAE, 2.6×90 cm: 0.1M $NH_4HCO_3$ pH 7.5, 100 ml/hr flow rate, 13 ml fractions, 206 nm detector. Fractions 105–130 were collected and lyophilized to give the title compound, 675 mg, as a colorless solid.

TLC: Silica Gel, 250$\mu$.

| Solvent | $R_f$ |
|---|---|
| 5:5:3:1 EtOAc:pyr:$H_2O$:HOAc | 0.59 |
| 4:1:5 nBuOH:HOAc:$H_2O$ | 0.40 |
| 15:3:12:10 nBuOH:HOAc:$H_2O$:pyr | 0.59 |

Amino Acid Analysis: Arg, 1.01; Pro, 1.00; Asp, 1.00; Val, 0.98; Phe, 1.00; peptide content: 78.5 percent.

EXAMPLE IV

Arginyl-Prolyl-Aspartyl-Valyl-Phenylalanine

The title peptide was synthesized by the solid phase method, starting with BOC-PHE Merrifield resin (8.06 g, 0.5/meq/g). The resin was sequentially coupled with three equivalents of BOC-VAL (once with DCC/4-pyrollidinopyridine, recoupled with DCC/HOBT), BOC-$\beta$-BZL-ASP (DCC/HOBT), BOC-PRO(DCC-/HOBT) and Ng-TOS-N$\alpha$-AOC-ARG(DCC/HOBT). The solvent was 4:1 $CH_2Cl_2$:DMF throughout.

Approximately ½ of this resin was dried and cleaved in HF (40 ml):anisole (10 ml):mercaptoethanol (1 ml) at 0° for 60 min. The residual solids were extracted with 10 percent HOAc and lyophilized to give 1.34 crude peptide.

The crude peptide was purified on Sephadex CM 25, 2.6×90 cm: gradient elution, 0.05M $NH_4OAc$ pH 5 (2.1 L) to 0.3M $NH_4OAc$ pH 5 (2.1 L), 100 ml/hr flow rate, 13 ml fractions, 206 nm detector. Fractions 61–100 were collected and lyophilized. The solid was chromatographed on a G-10 Sephadex column (eluted with 1 percent HOAc), collected and lyophilized to give the title compound, 780 mg.

TLC: Silica Gel G, 250$\mu$.

| Solvent | $R_f$ |
|---|---|
| 5:5:3:1 EtOAc:pyr:$H_2O$:HOAc | 0.38 |
| 4:1:5 n-BuOH:HOAc:$H_2O$, upper phase | 0.25 |
| 1:1 Trifluoroethanol:$NH_4OH$ | 0.71 |

Amino Acid Analysis: Arg, 1.00; Pro, 1.00; Asp, 1.00; Val, 1.03; Phe, 0.96; peptide content: 61 percent.

The above examples have been provided to illustrate the subject invention but not to limit its scope, which scope is set out only in the appended claims.

EXAMPLE IV

Arginyl-Lysyl-Aspartyl-Valyl-Histidine Solvated

The title compound was synthesized by the solid phase method starting with BOC-(im-TOS) Histidine attached to Merrifield resin at a substitution level of 0.21 mmole/gram. The wash sequence was as follows:

| | amt. × reps | time |
|---|---|---|
| 1 50 percent TFA/$CH_2Cl_2$ | 75 × 1 | 1 min |
| 2 50 percent TFA/$CH_2Cl_2$ | 75 × 1 | 20 min |
| 3 $CH_2Cl_2$ | 75 × 3 | 1 min |
| 4 25 percent $(CH_3)_2CHOH$/$CH_2Cl_2$ | 75 × 3 | 1 min |
| 5 $CH_2Cl_2$ | 75 × 3 | 1 min |
| 6 5 percent Diisopropyl-ethylamine/$CH_2Cl_2$ | 75/1 | 1 min |
| 7 $CH_2Cl_2$ | 75 × 3 | 1 min |
| 8 as in 6 | 75 × 1 | 1 min |
| 9 $CH_2Cl_2$ | 75 × 3 | 1 min |

-continued

| | amt. × reps | time |
|---|---|---|
| 10 Coupling step | | |

All couplings except Valine were carried out by the symmetrical anhydride technique. The symmetrical anhydride was synthesized by using the derivatized amino acid and DCC (2 to 1 molar ratio) in $CH_2Cl_2$ at 0° C. The dicyclohexylurea was removed by filtration and the filtrate added to the solid phase reaction vessel.

| Amino acid | Amount | mmoles | source | lot no. |
|---|---|---|---|---|
| Boc Valine | 4.0 g | 18.00 | Bachem | R4544 |
| Boc Valine | 4.0 g | 18.00 | Bachem | R4544 |
| Boc Valine | 2.0 g | 9.00 | Bachem | R4544 |
| Boc-β-benzyl-Asp | 3.22 g | 10.00 | Bachem | R5291 |
| $N^{\alpha}$-Boc-$N^{\epsilon}$-CBZ-Lys | 3.81 g | 10.00 | Bachem | R4651 |
| $N^{\alpha}$-CBZ-$N^{\gamma,\delta}$diCBZ-Arg | 2.9 g | 5.00 | Bachem | R5931 |

Notes:

1. Third coupling of BOC Valine was done using dicyclohexylcarbodiimide (9.00 mmoles) and 1-hydroxybenzotriazole monohydrate (9.00 mmoles) in dimethylformamide (20 ml)/methylene chloride (30 ml).

2. Following the third coupling of Boc Valine the resin peptide was acetylated with 5 percent acetic anhydride in $CH_2Cl_2$ (100 ml) with 100 mg of 4-dimethoxylaminopyridine.

3. The resin peptide was divided in half following the acetylation.

4. The resin peptide was split in half following the deprotection and neutralization of the lysine residue.

The yield of resin peptide was 6.7 g. The peptide was deprotected and removed from the resin by HF (60 ml) cleavage using anisole (3 ml) as a scavenger.

Following removal of the HF and anisole by reduced pressure the residue was triturated with diethyl ether, collected by filtration, washed with diethyl ether and extracted with 50 percent TFA/$CH_2Cl_2$ (4×25 ml). The extracts were combined, the solvents removed by reduced pressure and the residue triturated with diethyl ether. The resultant solid was collected by filtration, washed with diethyl ether and dried in vacuo at room temperature overnight to give 1.84 g of crude peptide.

1.0 g of crude peptide was chromatographed on Sephadex C-25 (2.6×95 cm) by elution with 0.2M $NH_4CH_3CO_2$ at pH 6.0. The flow rate was 90 ml/hr and fractions were collected every 7.5 minutes. After 200 fractions were collected the buffer was changed to 0.25M $NH_4CH_3CO_2$ at pH 7.0. Fractions 240 to 280 were pooled and lyophilized. The material was lyophilized twice from water to give 0.8 g. This was chromatographed on Sepahdex G-10 (2 tandem 2.6×95 cm columns) by elution with water. The flow rate was 40 ml/hr and fractions were 150 drops (6.5 ml). Fractions 78 to 87 were pooled and lyophilized to give 286 mg of the title compound.

TLC on silica gel G250 (J. T. Baker 5×20 cm). Spotted 40 μg.

| Solvent System | $R_f$ |
|---|---|
| n-Butanol/Acetic acid/Water (1:1:1) | 0.23 |
| n-Butanol/Acetic acid/Water/Pyridine (4:2:3:1) | 0.29 |
| Chloroform/Methanol/Conc. $NH_4OH$ (2:2:1) | 0.23 |

-continued

HPLC shows a purity of 99.4 percent

| Amino acid analysis | calculated | found |
|---|---|---|
| Arg | 1.0 | 1.03 |
| Lys | 1.0 | 1.00 |
| Asp | 1.0 | 0.95 |
| Val | 1.0 | 1.02 |
| His | 1.0 | 0.99 |

76.1 percent peptide

Optical rotation $[a]D^{22}$ = −32.9° (C = 0.1124 in 1 M HOAc)

EXAMPLE VI

Arginyl-Lysyl-Aspartyl-Valyl-Tryptophan Solvated

The peptide was synthesized using the DCC coupling technique with the following starting materials:

| | Amount | moles |
|---|---|---|
| Boc-Tryptophan (CHO)-resin ester | 6.0 g | 0.003 |
| Boc-Valine | 1.96 g | 0.009 |
| Boc-Aspartic acid-β-benzyl ester | 2.94 g | 0.009 |
| Boc-$N^{\epsilon}$-Lysine | 3.42 g | 0.009 |
| Boc-$N^{\gamma}$-Tosyl-Arginine | 3.86 g | 0.009 |
| Dicyclohexylcarboxiimide | 1.86 g | 0.009 |
| Hydroxybenzotriazole | 1.22 g | 0.009 |

The procedure for solid phase was as follows:

The resin was placed in a solid phase stirred reaction vessel and allowed to swell for four hours. The solvent was removed by filtration and the residue treated with 100 ml of the following solvents and reagents for the specified time and cycles. After each treatment, the liquid was removed by filtration.

| | |
|---|---|
| 1. $CH_2Cl_2$ | 3 × 1 minute - wash |
| 2. 50% TFA/$CH_2Cl_2$ | 1 minute - deblock |
| 3. 50% TFA/$CH_2Cl_2$ | 30 minutes - deblock |
| 4. $CH_2Cl_2$ | 3 × 1 minute - wash |
| 5. 5% N-Methylmorpholine/$CH_2Cl_2$ | 1 minute - neutralize |
| 6. $CH_2Cl_2$ | 3 × 1 minute - wash |
| 7. 5% N-Methylmorpholine/$CH_2Cl_2$ | 1 minute - neutralize |
| 8. $CH_2Cl_2$ | 3 × 1 minute - wash |
| 9. 5% Diisopropylethylamine/ $CH_2Cl_2$ | 0.5 minute - neutralize |
| 10. $CH_2Cl_2$ | 3 × 1 minute - wash |
| 11. 20% DMF/$CH_2Cl_2$ | 3 × 1 minute - wash |
| 12. Coupling | 1.5 to 4.0 hrs |
| 13. DMF | 3 × 1 minute - wash |

The peptide bond was formed by adding the blocked amino acid in 40 ml $CH_2Cl_2$ and HOBt in 20 ml DMF and stirring for 1 minute, then adding DCC in 40 ml $CH_2Cl_2$ and stirring for between 1.5 and 4.0 hours. The resin peptide was washed with DMF and $CH_2Cl_2$ after all couplings were complete and the Boc group was removed in the usual manner. The TFA salt was washed well with $CH_2Cl_2$ and removed from the reaction vessel and dried to a constant weight in vacuo, 8.69 g.

The peptide was cleaved from the resin by stirring in liquid HF (with anisole and tryptophan added) for 1 hour at 0° C. The HF was removed at reduced pressure. The solid was washed with ether and the peptide was extracted from the resin with 25 percent HOAc/$H_2O$. This material was lyophilized to give 3.45 g. crude product with the formyl group still on tryptophan. The material was deformylated by stirring in 1.0M $NH_4HCO_3$ pH 9.0 (100 ml) for 24 hours. The crude material was lyophilized and chromatographed on a Sephadex SP-C-25 column (2.6×90 cm). Elusion with 0.2M $NH_4OAc$ pH 6.00 gave after combining the appropriate fractions and lyophilizing, 2.09 g. product (93% pure). This material was prep.-HPLC on a M-20 column (Whatman ODS-3) and eluted with 0.01M $NH_4OAc$, 12% $CH_3CN$ pH 5.00 to give after combining the appropriate fractions, 0.75 g pure product.

EXAMPLE VII

Acetyl-Arginyl-α-Aminoisobutyryl-Aspartyl-Valyl-Phenylalaminamide, solvated

A. TFA Asp(OBzl)-Val-Phe-NH-MBHA—resin p-methylbenzhydrylamine-resin (70 g; 0.3 mmoles/g resin) was swelled in $CH_2Cl_2$ for 1 h. Boc-Phe, Boc-Val and Boc-Asp(OBzl)-OH were incorporated to the resin via DCC-mediated coupling. After removal of the N-terminal Boc-group, the peptide-resin was dried and used for synthesis of other peptides.

B. Ac-Arg-Aib-Asp-Val-Phe-$NH_2$

TFA Asp(OBzl)-Val-Phe-NH-MBHA—resin (6 g) was coupled with Boc-Aib and Aoc-Arg(Tos)—OH using DCC/HOBt coupling, consecutively. After removal of the Aoc-group of Arg, the peptide-resin was acetylated with $Ac_2O$/pyridine (1:1). The peptide-resin (5 g) was then cleaved with HF/Anisol (9:1; 50 ml) at 0° C. for 1 hr. The peptide was extracted with 5 percent $HOAc/H_2O$ (3×50 ml) and lyophilized to give 570 mg of solid material. The crude peptide was chromatographed on a Sephadex DEAE-Column (80 cm×2.5 cm) equilibrated with unbuffered 0.05M$(NH_4)HCO_3$. The flow rate was 85 ml/hr and fractions of 10 ml were collected. The peptide eluted between tubes 35–48 and this fraction was then lyophilized to give 450 mg of product.

Thin layer chromatography (Silica Gel $F_{60}$; 200 microns). $R_{fI}$ 0.45 ($NH_4OH$/Isopropanol=37:84). $R_{fII}$ 0.25 (n-BuOH/HOAc/$H_2O$=3:1:1).

Amino Acid Analysis: Arg, 1.01; Aib, 1.03; Asp, 1.03; Val, 0.99; Phe, 1.00. Peptide content: 88.3 percent.

EXAMPLE VIII

Acetyl-Arginyl-Prolyl-Aspartyl-Valyl-Phenylalanineamide, solvated

Ac-Arg(Tos)-Pro-Asp(OBzl)-Val-Phe-NH-MBHA—resin was synthesized by SPPS starting with 10 g of p-methylbenzhydrylamine-resin (subst. 0.3 mmoles $NH_2$/g resin). The amino acid derivatives and DCC were used in 3 fold excess for the following couplings: Aoc-Arg(TOS)-OH, Boc-Pro, Boc-Asp(OBzl)-OH, Boc-Val and Boc-Phe. The peptide-resin (4 g) was then cleaved with HF/Anisol (9:1, 40 ml) for 1 h at 0° C. After removal of the HF/anisol, the mixture was filtered and washed with ether (3×30 ml). The peptide was extracted with 5 percent $HOAc/H_2O$ (3×50 ml) and lyophilized to give 315 mg of product. The crude peptide was then purified on a Sephadex DEAE Column (2.5 cm×80 cm) equilibrated with 0.5M$(NH_4HCO_3)$ (unbuffered). The flow rate was 85 ml/h and fractions of 12 ml/tube were collected. The desired peptide eluted between tubes 30–40. This fraction was lyophilized to give 300 mg of material.

Thin layer chromatography (Silica Gel $F_{60}$; 200 microns). $R_{fI}$ 0.55 ($NH_4OH$/Isopropanol=37.84). $R_{fII}$ 0.3 (n-BuOH/HOAc/$H_2O$=3:1:1).

Amino Acid Analysis: Arg, 1.00; Pro, 0.99; Asp, 0.99; Val, 1.00; Phe, 1.00. Peptide content: 57.5 percent.

EXAMPLE IX

Arginyl-Lysyl-Glutamyl-Valyl-Histidine Solvated

The compound was synthesized by the solid phase method starting with 5.0 g of Boc-(im-Tos) Histidine attached to Merrifield resin at a substitution level of 0.21 mmole/gram. The wash sequence was as follows:

| | amt. × reps | time |
|---|---|---|
| 1 50 percent TFA/$CH_2Cl_2$ | 75 × 1 | 1 min |
| 2 50 percent TFA/$CH_2Cl_2$ | 75 × 1 | 20 min |
| 3 $CH_2Cl_2$ | 75 × 3 | 1 min |
| 4 25 percent $(CH_3)_2CHOH$/$CH_2Cl_2$ | 75 × 3 | 1 min |
| 5 $CH_2Cl_2$ | 75 × 3 | 1 min |
| 6 5 percent Diisopropylethylamine/$CH_2Cl_2$ | 75 × 1 | 1 min |
| 7 $CH_2Cl_2$ | 75 × 3 | 1 min |
| 8 as in 6 | 75 × 1 | 1 min |
| 9 $CH_2Cl_2$ | 75 × 3 | 1 min |
| 10 Coupling step | | |

All couplings were carried out by using euqal molar amounts of the protected amino acid, dicyclohexylcarbodiimide and hydroxybenzotraizole. The solvent used was a mixture of dimethylformamide (12 ml) and methylene chloride (38 ml).

| Amino Acid | A-mount | mmoles | source | lot no. |
|---|---|---|---|---|
| Boc Valine | 0.65 g | 3.00 | Peninsula | 001678 |
| Boc-benzyl-Glu | 1.01 g | 3.00 | Bachem | R4835 |
| $N^{\alpha}$-Boc-$N^{\gamma}$-CBZ-Lys | 1.14 g | 3.00 | Bachem | R4651 |
| $N^{\alpha}$-CBZ-$N^{\gamma,\Delta}$diCBZ-Arg | 1.14 g | 3.00 | Bachem | R5931 |

Notes:

Following the final coupling the resin-peptide was washed with dimethylformamide (2×50 ml), isopropanol (2×50 ml) and dried in vacuo at 50° C. for 20 hrs.

The yield of resin peptide was 6.9 g. 6.7 g of resin peptide was deprotected and removed from the resin by HF (50 ml) cleavage using anisole (1 ml) as a scavenger.

Following removal of the HF and anisole by reduced pressure the residue was triturated with diethyl ether, collected by filtration, washed with diethyl ether and extracted with 5 percent acetic acid/water (4×25 ml) and then water (4×25 ml). The extracts were combined and lyophilized to give 1.1 g of crude peptide.

1.0 g of crude peptide was chromatographed on Sephadex C-25 (2.6×95 cm) by elution with 0.25M $NH_4HCO_3$ at pH 7.0. The flow rate was 100 ml/hr and fractions were collected every 200 drops. Fractions 161 to 210 were pooled and lyophilized. The material was lyophilized thrice from water to give 568 mg of the title compound.

Analytical Data: TLC on silica gel G250 (J. T. Baker 5×20 cm).

| Solvent system | $R_f$ |
|---|---|
| n-Butanol/Acetic acid/Water (1:1:1) | 0.29 |
| n-Butanol/Acetic acid/Water/Pyridine (4:2:3:1) | 0.32 |
| Chloroform/Methanol/Conc. $NH_4OH$ (2:2:1) | 0.30 |

| Amino acid analysis | calculated | found |
|---|---|---|
| Arg | 1.0 | 1.05 |
| Lys | 1.0 | 1.01 |
| Glu | 1.0 | 1.02 |
| Val | 1.0 | 0.99 |
| His | 1.0 | 0.93 |

-continued

| |
|---|
| 74.7 percent peptide |
| Optical rotation $[a]D^{22}$ = −24.3° (C = 0.1154 in .1 M HOAc) |

EXAMPLE X

Arginyl-Lysyl-Aspartyl-Valyl-Proline

The title compound was prepared by the solid phase method, starting with Boc-Pro benzyl ester resin (5.08 g, 0.64 meq/g). The following standard routines were used:

| | |
|---|---|
| Deprotection: | 50 ml 50% TFA/$CH_2Cl_2$ for 5 min, then 50 ml 50% TFA/$CH_2Cl_2$ for 20 min; |
| Washing: | 50 ml $CH_2Cl_2$ twice for 1 min each, followed by 50 ml iPrOH for 1 min, then 50 ml $CH_2Cl_2$ twice for 1 min each; |
| Neutralization: | 50 Ml 5% DIEA/$CH_2Cl_2$ twice for 2.5 min each; |
| Coupling, Method 1: | 15.0 mmol of the protected amino acid and HOBT (2.3 g) were dissolved in 10 ml DMF and then diluted with 30 ml $CH_2Cl_2$. DCC (3.09 g) was dissolved in 10 ml $CH_2Cl_2$, added to the mixture of reactants and resin and agitated for 2–2.5 h. |
| Coupling, Method 2: | 15.0 mmol of the protected amino acid hydroxy-succinimide ester was dissolved in 50 ml $CH_2Cl_2$. NMM (3.3 ml) was added and the mixture agitated with the resin for 18 h. |

In sequence, the resin was coupled once each with Boc-Val (Method 1) and Boc-Bzl$\beta$-Asp-OSu (Method 2). Half the resin (3942-137B') was withdrawn and the remainder coupled once each with Boc$\alpha$-Cbz$\epsilon$-Lys and $(Cbz)_3$Arg (both by Method 1). The resin was washed, air-dried and cleaved in HF/anisole (30 ml/8 ml) for 60 min at 0° C.

The resin residue was quenched in $Et_2O$ and filtered. The solids were extracted with 10% HOAc (100 ml) for 1 h, filtered, and the extract lyophilized to give the hydrofluoride salt as a colored gum, 1.09 g.

The crude peptide was purified on CM Sephadex (2.6×87 cm column, 0.15M $NH_4OAc$, unbuffered; 100 ml/h flow rate, 12 ml/fraction, 225 nm detector). Fractions 203–235 were pooled and lyophilized to give 880 mg of the title compound.

II. Analysis:

| Amino Acid | Ratio |
|---|---|
| Arg | 1.01 |
| Pro | 0.99 |
| Asp | 1.00 |
| Val | 0.96 |
| Tyr | 1.03 |
| 56.7% peptide content | |
| Thin Layer Chromatography | 250 micron, Silica Gel G |

| Elutent | $R_f$ | |
|---|---|---|
| 1:1:1:1 | n-BuOH:HOAc:$H_2O$:EtOAc | 0.19 |
| 15:3:12:10 | n-BuOH:HOAc:$H_2O$:Pyridine | 0.34 |
| 5:1:3:5 | EtOAc:HOAc:$H_2O$:Pyridine | 0.27 |

EXAMPLE XI

Arginyl-Lysyl-Glutamyl-Valyl-Tryptophan Solvated

The peptide was synthesized using the DCC coupling technique with the following starting materials:

| | Source | Amount | Moles |
|---|---|---|---|
| Boc-Tryptophan (CHO)-resin ester | — | 6.0 g | 0.003 |
| Boc Valine | Bachem | 1.96 g | 0.009 |
| Boc Glutamic acid-8-benzyl ester | Bachem | 3.04 g | 0.009 |
| Boc-N$^{\epsilon}$-Z-Lysine | Bachem | 3.42 g | 0.009 |
| Boc-N$^{\gamma}$-Tosyl-Arginine | Bachem | 3.86 g | 0.009 |
| Dicyclohexylcarbodiimide | Chemalog | 1.86 g | 0.009 |
| Hydroxybenzotriazole | Aldrich | 1.22 g | 0.009 |

The procedure for solid phase was as follows:

The resin was placed in a solid phase stirred reaction vessel and allowed to swell for four hours. The solvent was removed by filtration and the residue treated with 100 ml. of the following solvents and reagents for the specified time and cycles. After each treatment, the liquid was removed by filtration.

| | |
|---|---|
| 1. $CH_2Cl_2$ | 3 × 1 minute - wash |
| 2. 50 percent TFA/$CH_2Cl_2$ | 1 minute - deblock |
| 3. 50 percent TFA/$CH_2Cl_2$ | 30 minutes - deblock |
| 4. $CH_2Cl_2$ | 3 × 1 minute - wash |
| 5. 5 percent N-Methyl-morpholine/$CH_2Cl_2$ | 1 minute - neutralize |
| 6. $CH_2Cl_2$ | 3 × 1 minute - wash |
| 7. 5 percent N-Methyl-morpholine/$CH_2Cl_2$ | 1 minute - neutralize |
| 8. $CH_2Cl_2$ | 3 × 1 minute - wash |
| 9. 5 percent Diisopropyl-ethylamine/$CH_2Cl_2$ | 0.5 minute - neutralize |
| 10. $CH_2Cl_2$ | 3 × 1 minute - wash |
| 11. 20 percent DMF/$CH_2Cl_2$ | 3 × 1 minute - wash |
| 12. Coupling | 1.5 to 4.0 hrs. |
| 13. DMF | 3 × 1 minute - wash |

The peptide bond was formed by adding the blocked amino acid in 40 ml $CH_2Cl_2$ and HOBt in 20 ml DMF and stirring for 1 minute, then adding DCC in 40 ml $CH_2Cl_2$ and stirring for between 1.5 and 4.0 hours. The resin peptide was washed with DMF and $CH_2Cl_2$ after all couplings were complete and the Boc group was removed in the usual manner. The TFA salt was washed well with $CH_2Cl_2$ and removed from the reaction vessel and dried to a constant weight in vacuo, 8.75 g.

The peptide was cleaved from the resin by stirring in liquid HF (with anisole and tryptophan added) for 1 hour at 0° C. The HF was removed at reduced pressure. The solid was washed with ether and the peptide was extracted from the resin with 25 percent HOAc/$H_2O$. This material was lyophilized to give 3.60 g crude product with the formyl group still on tryptophan. The material was deformylated by stirring in 1.0M $NH_4HCO_3$ pH 9.0 (100 ml) for 24 hours. The crude material was lyophilized and chromatographed on a Sephadex SP-C-25 column (2.6×90 cm). Elusion with 0.1M $NH_4OAc$ pH 5.38 gave after combining the appropriate fractions and lyophilizing, 2.10 g product (~96 percent pure).

The material was purified on a Whatman ODS-3 NPLC column and eluted with 0.01M $NH_4OAc$, 12 percent $CH_3CN$ pH 5.00 to give after combining the appropriate fractions, 0.90 g pure product.

TLC: Rf (solvent system). $Rf_1$ 0.15 (BuOH:HOAc:$H_2O$ 3:1:1). $Rf_2$ 0.28 (BuOH:HOAc:$H_2O$:EtOAc 1:1:1:1). $Rf_3$ 0.09 ($CHCl_3$:MeOH:$NH_4OH$ 12:9:4).

Amino Acid Analysis: Arg (0.99) Lys (0.98) Glu (0.97); Val (1.05) Trp (0.96).

Percent composition = 88.4 percent peptide.

EXAMPLE XII

Arginyl-Lysyl-Glutamyl-Valyl-Tryptophan amide Solvated

The compound was synthesized by the solid phase method starting with the resin-peptide Val-Trp-NH-benzyhydryl-amine resin.

| Amino acid | A-mount | mmoles | source | lot no. |
|---|---|---|---|---|
| Boc-γ-benzyl-Glu | 2.23 g | 16.50 | Bachem | R5785 |
| $N^{\alpha}$-Boc-$N^{\epsilon}$-CBZ-Lys | 6.29 g | 16.50 | Bachem | R5268 |
| $N^{\alpha}$-CBZ-$N^{\gamma,\Delta}$-di-CBZ-Arg | 9.53 g | 16.50 | Bachem | R5931 |

1. Following the coupling of $N^{\alpha}$-Boc-$N^{\epsilon}$-CBZ-Lys the resin peptide was acetylated with 5 percent acetic anhydride in $CH_2Cl_2$ (100 ml) with 100 mg of 4-dimethylaminopyridine.

The yield of resin peptide was 15.3 g. 9.0 g of the resin peptide was deprotected and removed from the resin by HF (80 ml) cleavage used anisole (9 ml) as a scavenger. The solvents were removed by reduced pressure and the residue triturated with diethyl ether. The solids were collected by filtration and extracted with 5 percent acetic acid in water (4×50 ml). The extracts were combined and lyophilized to give 1.4 g of crude product.

The crude material was dissolved in 250 ml of 1.0M $NH_4HCO_3$ and the pH adjusted to 9.5. This solution was allowed to stand for 24 hrs at room temperature and then lyophilized to give 1.2 g of crude product.

The crude peptide was chromatographed on Sephadex C-25 (2.6×90 cm) by elution with 0.3M $NH_4OAc$ pH 6.0 with a flow rate of 150 ml/hr and fractions of 20 ml. Tubes 90 to 110 were shown to contain pure product by HPLC and were pooled and lyophilized to give 450 mg of the title compound.

Analytical Data: TLC on silica gel GF 250 microns.

| Solvent system | $R_f$ |
|---|---|
| n-Butanol/Acetic acid/Water (1:1:1) | 0.13 |
| n-Butanol/Acetic acid/Water/Ethyl Acetate (1:1:1:1) | 0.10 |
| HPLC shows a purity of 99.1 percent | |

| Amino acid analysis | calculated | found |
|---|---|---|
| Arg | 1.0 | 1.02 |
| Lys | 1.0 | 0.96 |
| Glu | 1.0 | 0.99 |
| Val | 1.0 | 1.04 |
| Trp | 1.0 | 0.94 |

8.21 percent peptide.

Optical rotation $[\alpha]_D = -20.7°$ (C=0.997 in 0.1M HOAc).

EXAMPLE XIII

Arginyl-Lysyl-Aspartyl-Valyl-Tryptophan amide Solvated

The compound was synthesized by the solid phase method starting with benzhydrylamine resin at a substitution level of 0.68 meq/gram. The wash sequence was as follows:

| | amt. × reps | time |
|---|---|---|
| 1 $CH_2Cl_2$ | 100 × 3 | 2 min |
| 2 50 percent TFA/$CH_2Cl_2$ | 100 × 1 | 2 min |
| 3 50 percent TFA/$CH_2Cl_2$ | 100 × 1 | 20 min |
| 4 $CH_2Cl_2$ | 100 × 3 | 2 min |
| 5 33 percent $(CH_3)_2CHOH/CH_2Cl_2$ | 100 × 3 | 2 min |
| 6 $CH_2Cl_2$ | 100 × 3 | 2 min |
| 7 6.5 percent Diisopropyl-ethylamine/$CH_2Cl_2$ | 100 × 1 | 4 min |
| 8 $CH_2Cl_2$ | 100 × 3 | 2 min |
| 9 as in 7 | 100 × 1 | 4 min |
| 10 $CH_2Cl_2$ | 100 × 3 | 2 min |
| 11 Coupling step | | |
| 12 Dimethylformamide | 100 × 1 | 2 min |
| 13 $CH_2Cl_2$ | 100 × 3 | 2 min |

All couplings were done with equal molar amounts of the protected amino acid, dicyclohexylcarbodiimide and hydroxybenzotriazole. The couplings used dimethylformamide (20 ml) and methylene chloride (60 ml) as solvents.

| Amino Acid | A-mount | mmoles | source | lot no. |
|---|---|---|---|---|
| Boc-Trp(CHO) | 10.97 g | 33.00 | Peninsula | 000613 |
| Boc-Valine | 7.17 g | 33.00 | Bachem | R4544 |
| Boc-β-benzyl-Asp | 5.32 g | 16.50 | Bachem | R5291 |
| Nα-Boc-$N^{\epsilon}$-CBZ-Lys | 6.20 g | 16.50 | Bachem | R5268 |
| Nα-CBZ-$N^{\gamma,\Delta}$ diCBZ-Arg | 9.53 g | 16.50 | Bachem | R5931 |

1. The resin peptide was split in half following the deprotection and neutralization of the Valine residue.

2. Following the coupling of $N^{\alpha}$-CBZ-$N^{\gamma,\Delta}$-diCBZ-Arg the resin peptide was acetylated with 5 percent acetic anhydride in $CH_2Cl_2$ (100 ml) with 100 mg of 4-dimethylaminopyridine.

The yield of resin peptide was 15.7 g. 7.0 g of the resin peptide was deprotected and removed from the resin by HF (60 ml) cleavage using anisole (5 ml) as a scavenger. The solvents were removed by reduced pressure and the residue triturated with diethyl ether. The solids were collected by filtration and extracted with 5 percent acetic acid in water (5×20 ml). The extracts were combined and lyophilized to give 1.2 g of crude product.

The crude material was dissolved in 250 ml of 1.0M $NH_4HCO_3$ and the pH adjusted to 9.5. This solution was allowed to stand for 24 hrs at room temperature and then lyophilized to give 1.2 g of crude product.

The crude peptide was chromatographed on Sephadex C-25 (2.6×90 cm) by elution with 0.3M $NH_4OAc$ pH 6.0 with a flow rate of 150 ml/hr and fractions of 20 ml. Tubes 197 and 221 were shown to contain pure product by HPLC and were pooled and lyophilized to give 450 mg of the title compound.

Analytical Data: TLC on silica gel GF 250 microns.

| Solvent system | $R_f$ |
|---|---|
| n-Butanol/Acetic acid/Water (1:1:1) | 0.13 |
| n-Butanol/Acetic acid/Water/Ethyl Acetate (1:1:1:1) | 0.10 |

| Amino acid analysis | calculated | found |
|---|---|---|
| Arg | 1.0 | 1.00 |
| Lys | 1.0 | 0.97 |
| Asp | 1.0 | 0.98 |
| Val | 1.0 | 1.06 |

-continued

| | | |
|---|---|---|
| Trp | 1.0 | 0.96 |
| 75.1 percent peptide | | |
| Optical rotation [a]D = −35.6° (C = 1.002 in M HOAC) | | |

EXAMPLE XIV

$N^{\alpha}$-Acetyl-Arginyl-3,4-dehydro-Prolyl-Aspartyl-Valyl-Tyrosineamide

A. BOC-3,4-dehydro-Proline 3,4-dehydro-Pro (200 mg; 1.76 mmoles) was dissolved in dioxane/$H_2O$ (8 ml; 2:1). To this solution, 1N NaOH (1.8 ml) and di-t-Butyldicarbonate (436 mg; 2 mmoles) were added at 0° C. with stirring. The mixture was then stirred at room temperature overnight. Dioxane was removed and to the remaining water phase, ethyl acetate (20 ml) was added. The mixture was cooled in an ice bath, acidified to pH 2.0 with 0.5N HCl and transferred into separation funnel. The organic layer was separated and the aqueous layer was extracted twice with EtOAc (2×20 ml). The combined organic phase was dried over $Na_2SO_4$ and filtered. The solvent was removed and the remaining residue was dried and used without further purification.

$^1$HNMR of the sample ($CDCl_3$; Ar No. 5030-83) indicated the presence of BOC-group at 1.45 ppm.

B. $N^{\alpha}$-Acetyl-Arginyl-3,4-dehydro-Prolyl-Aspartyl-Valyl-Tyrosineamide

The peptide was synthesized on a (p-methyl)benzhydrylamine-resin (2 g resin; substitution of 0.25 mmoles of $NH_2$ of g resin) by solid-phase method. The incorporation of BOC-Tyr(Bzl)-OH, Boc-Val, BOC-3,4-dehydro-Pro and Aoc-Agr(Tos)-OH was carried out via DCC-coupling. The coupling was monitored by qualitative ninhydrin test. The acetylation of Arginine was carried out with 50 percent acetic anhydride/pyridine (15 ml) and DMAP (15 mg). The peptidyl resin was then washed thoroughly with DMF and $CH_2Cl_2$ and dried. The dried peptidyl resin (2 g) was cleaved with HF/anisole (20 ml; 9:1) at 0° C. for 1 h. The peptide-resin mixture was washed with ether (3×20 ml) and the peptide was extracted with 5 percent HOAc/$H_2O$ (200 ml). After lyophilization, the peptide was applied into a Sephadex SPC-25 column (50 cm×0.9 cm) and equilibrated with 0.02M $NH_4OAc$; pH 4.6. The flow rate was 80 ml/hr and fractions of 12 ml were collected. The product was eluted between tubes 22–39, which were pooled and lyophilized.

The lyophilized material was purified again on Sephadex SPC-25 column (60 cm×2.5 cm) equilibrated with 0.02M $NH_4OAc$; pH 4.5–6.8 under the same condition as described above. The peptide was eluted between tubes 55–75, which were pooled and lyophilized to give 80 mg of product.

Rf 0.45 (n-BuOH/HOAc/$H_2O$/Pyr=15:3:12:10; Silica Gel F60). Rf 0.27 (n-BuOH/HOAc/$H_2O$-3:1:1; Silica Gel F60).

Amino Acid Analysis: Asp, 1.04; Val, 1.00; Tyr, 0.85; Arg, 0.96; 3,4-dehydro-Pro, 1.08; Peptide content: 72 percent; hygroscopic material.

HPLC: Whatman Partisil-ODS column. 10 percent $CH_3CN$/0.02M $NH_4OAc$; pH 4.6. Flow rate: 2 ml/min. The peptide was 99.7 percent pure and has a retention time of 14.3 min.

EXAMPLE XV

Cyclic-GMP Assay

This assay measures the ability of the test peptide to bind to the cell membrane receptor of the intact CEM cell and selectively stimulate production of cyclic-GMP, as does thymopoietin itself.

The CEM cell line was obtained from the American Type Culture Collection and was cultured in RPMI-1640 medium supplemented with 10% heat-inactivated fetal bovine serum, 10% heat-inactivated horse serum, 2 mM L-glutamine, and 50 g/ml gentamycin at 37° C. in a humid atmosphere containing 5 percent $CO_2$, to a final density of $3–4\times10^6$ cells/ml. At this concentration, the cells were in the early stationary phase of the growth curve and were judged greater than 90% viable by trypan blue exclusion. The cells were grown for four days and harvested. After harvesting, the cells were washed three times in PBS and were resuspended in RPMI-1640 medium at a concentration of $3.12\times10^7$ cells/ml. After the cells had been allowed to equilibrate at 37° C. for 30 min, various concentrations of the test peptides were added in a volume of 25 μl of medium to 1 ml of cells, the initial concentration of test compound added being selected to yield the desired final concentration of test peptide in the medium. The test peptide was mixed instantly with the cell suspension. The incubation was allowed to proceed in a shaking water bath at 37° C. for 4–5 min and was then terminated by addition of ice-cold trichloroacetic acid (10%; 1 ml).

The cells in TCA were then homogenized and sonicated to release cyclic nucleotide. The resulting suspension was centrifuged at 3000 g for 20 min at 4° C. and the resulting precipitate was dissolved in 0.1N NaOH and sonicated for a further 30 minutes, after which the protein content was determined by the method of Cadman, et al., Anal. Biochem., 96, 21–23 (1979). The TCA was removed from the supernatant fraction by extracting four times with 5 ml of water-saturated diethyl ether. After the final extraction, the remaining traces of ether were removed from the supernatant fraction by heating it for 10 min in a 50° C. water bath. After lyophilization of the extracted supernatant fraction, it was reconstituted in 50 mM acetate buffer, ph 6.2, for radioimmunoassay of cyclic nucleotide using the assay kit NEX-133, New England Nuclear, Boston, Mass. 02113.

A conventional competition radioimmunoassay against radio labelled cyclic GMP was conducted to determine the amount of cyclic GMP induced by each concentration of test peptide. Results are shown in FIG. 1 and in the following table, in which representative subject peptides have been assayed in comparison with thymopentin (designated "TP-5") and a "nonsense" peptide H-ASP-ARG-TYR-LYS-VAL-OH. These results demonstrate the superior potency of the subject peptides compared to thymopentin and also indicate the specificity of the assay for peptides having thymopentin-like activity.

TABLE 1

| | Concentration of c-GMP Produced (picomoles/ml) | | | | | |
|---|---|---|---|---|---|---|
| | Concentration of Peptide (μg/ml) | | | | | |
| | $10^0$ | $10^1$ | $10^2$ | $10^3$ | $10^4$ | $10^5$ |
| (S—ASP—VAL—TYR—OH (TP-5) | 0 | 4.5 | 9 | 12 | 14 | — |
| α-acetyl-ARG—PRO—ASP—VAL—PHE—OH | 7 | 15 | — | — | — | — |
| o-formyl-ARG—PRO—ASP—VAL—PHE—OH | 0 | 14 | — | — | — | — |
| H—ARG—PRO—ASP—VAL—PHE—OH | 0 | 12 | — | — | — | — |
| H—ARG—LYS—ASP—VAL—HIS—OH | 0 | 9 | — | — | — | — |
| H—ARG—LYS—ASP—VAL—PHE—OH | 6 | 9 | — | — | — | — |
| H—ASP—ARG—TYR—LYS—VAL—OH | — | — | — | 0 | 0 | 0 |

Other representative compounds demonstrating superior results on this assay were: H-ARG-LYS-ASP-VAL-TRP-OH; N-α-acetyl-ARG-PRO-ASP-VAL-PHE-$NH_2$; N-α-acetyl-ARG-AIB-ASP-VAL-PHE-$NH_2$; H-ARG-LYS-ASP-VAL-TRP-$NH_2$; and N-α-acetyl-ARG-3,4-dehydro-PRO-ASP-VAL-TYR-$NH_2$.

EXAMPLE XVI

Receptor Assay

This assay measures the ability of the test peptide to compete with labelled thymopoeitin to bind to the isolated thymopoietin cell surface receptor protein from CEM cells.

Materials—CEM cell lines were obtained from the American Type Culture Collection. 3-Nitro-2-pyridine sulfonyl chloride and 2-pyridinethiol 1-oxide were provided by Dr. Rei Matseuda, Sanyo Laboratories, Tokyo. RPM1-1640, fetal bovine serum and L-glutamine were obtained from Gibco, gentamycin from Schering, and lectin-coupled agarose beads from Vector Laboratories. Sephadex was purchased from Pharmacia Fine Chemicals. and human IgG from Miles Laboratories. All other chemicals were purchased from common commercial sources and were of reagent grade. Rabbit anti-thymopoeitin antibody and ubiquitin were produced following known techniques.

The abbreviations used are: PBS, phosphate-buffered saline; TCA, trichloroacetic acid, SDS, sodium dodecylsulfate; Con A, concanavilin A; TP, thymopoietin; PEG, polyethylene glycol; BSA, bovine serum albumin; I.P., intraperitoneal; PMSF, phenyl methyl sulfonyl fluoride; FTS, facteur thymique serique; CRF, corticotropin-releasing factor; ACTH, adrenocorticotropic hormone; Hepes, N-2-hydroxyethylpiperazine N-2-ethane-sulfonic acid.

Preparation of Membrane Glycoprotein—The CEM human lymphoid cell line was cultured in RPMI-1640 supplemented with 10 percent heat-inactivated fetal bovine serum, 2 mM L-glutamine and 50 μg/ml gentamycin at 37° C. in a humid atmosphere containing 5 percent $CO_2$, to a final density of $3\text{–}4\times10^6$ cells/ml. At this concentration, cells were in the early stationary phase of the growth curve and were judged greater than 90 percent viable by trypan blue exclusion.

Membrane glycoproteins were prepared by a modification of the technique of Hedo, et al., Biochem, 20, 3385–3393 (1981). The cells were washed once with PBS and were suspended in 40 percent sucrose, 50 50 mM Hepes, 1 percent EDTA, 0.1 percent O-phenanthroline, and 1 mM PMSF (in methanol), pH 7.8, and homogenized in a glass homogenizer at room temperature. The total suspension was then subjected to sonication by a cell disruptor sonicator with a cup horn attachment (Model W-225R) at 35° C. for 10 min. The suspension was centrifuged at 600×g for 10 min at 4° C. in a Sorval GLC-3 centrifuge, and the supernatant was recentrifuged at 20,000×g in a Sorval 5B centrifuge at 4° C. for 3 min. The crude membrane fraction obtained from this pellet was suspended in 50 mM Hepes, 10 mM $MgSO_4$, and 1 mM PMSF, pH 7.8, at a final protein concentration of 5 mg/ml. Solubilization of protein was performed by stirring the suspension for 2 h at 25° C. in the presence of 1 percent Triton X-100 (final concentration) and 0.1 percent brij-96 (polyoxyethylene 10, oleyl ether) (final concentration). The suspension was centrifuged at 200,000×g for 2 h at 4° C., and the supernatant was stored at −70° C. Soluble protein concentration was measured according to the technique of Cadman, et al., using BSA as a standard and buffer as a control.

Wheat germ agglutinin or ricinus communis agglutinin-I was used for purification of the receptor protein. All lectin beads were stored at 4° C. with their corresponding monosaccharide inhibitors (300 mM).

For each purification 2 ml of lectin-agarose was packed into a 1 cm diameter column and washed at room temperature with 25 ml of 0.15M NaCl, 50 mM Hepes, 0.1 percent Triton X-1 and 0.01 percent SDS, pH 7.8.

The columns were washed with 200 ml of 0.15M NaCl, 50 mM Hepes and 0.1 percent Triton X-100, pH 7.8, followed by a final wash of this buffer containing 10 mM $MgSO_4$. PMSF (1 mM) was added to all the buffer systems. Solubilized membrane proteins (~10 mg) were recycled five times through individual columns. The column was then washed with 100 ml of 0.15M NaCl, 50 mM Hepes, 10 mM MgSO and 0.1 percent Triton X-100, pH 7.8, at 4° C. Monosaccharide inhibitors, at a concentration of 400 mM in 3 ml washing buffer, were used for individual column elutions; N-acetyl glucosamine for wheat germ agglutinin and β-methyl D-galactoside for ricinus communis agglutinin-I. The monosaccharides were applied to the column, which was stopped for 30–40 min to permit equilibration and then eluted further. The protein eluate was dialyzed against 500 ml of 50 mM Hepes, 10 mM $MgSO_4$ and 0.1 percent Triton X-100, pH 7.8, at 4° C.

Preparation of Radiolabelled Thymopoietin—Thymopoietin was dissolved in 0.2M sodium carbonate-bicarbonate buffer, pH 9.8, to obtain reactive amino groups. 3-nitro-2-pyridine sulfonyl chloride in dioxane (10:1 moles) were added to the thymopoietin solution and stirred for 5 h at 20° C. After the addition of water, the insoluble material was centrifuged. The protected peptide was purified using Sephadex G-25 chromatography followed by digestion with post-proline cleaving enzyme to remove the $NH_2$-terminal blocked proline. Methyl 3,5 di[$^{125}$I]iodohydroxybenzimidate (4000 Ci/mM) was obtained at a concentration of 5.5 mCi/ml in methanol and was evaporated to dryness. The iodinated imidoester (1.4 nM) was reacted with protected thymopoietin (5 μg; 0.9 nM) according to the method of Wood, et al., Anal. Biochem., 69, 339-349 (1975), with the following modifications. The reaction was carried out in 500 μl of 0.16M borate buffer, pH 9.1, for 24 h at 4° C. The reaction was stopped by the addition of 500 μl of 2M citrate phosphate buffer, pH 5.5, at 4° C. The sample was chromatographed on a Biogel P-10 column in sodium pyrophosphate, pH 7.5 (15 drops/fraction), at 4° C. to separate the free iodine.

The iodinated peptide was dissolved in water and treated with 2-pyridinethiol 1-oxide (10:1 moles) for 5 h at room temperature to remove the protecting groups. The deprotected labelled peptide was purified on a Biogel P-10 column. Three radioactive peaks were obtained, the first two of which were immunoactive with rabbit antihymopoietin antibody. The first peak was then applied to a 1×60 cm column of DEAE-Sephadex A-25 that had been equilibrated with 50 mM Tris buffer, pH 7.0. The iodination mixture was eluted with this buffer using a linear gradient of increasing ionic strength from the equilibration concentrations up to 1.0M. The radioactivity of each fraction was determined using an LKB 1280 Ultra gamma spectrometer.

Fractions with peak radioactivity from each purification scheme were analyzed for binding with excess antihymopoietin antibody. Fractions from peak II (fractions 35-45) of the DEAE-Sephadex A-25 column showed the highest specific binding and were used subsequently in the radioreceptor assay.

Iodinated thymopoietin retained biological activity as determined by assessing its effect in a neuromuscular assay (Goldstein, Nature, 247, 11-14 (1974)) and its effect on the synthesis of cyclic GMP by CEM cells.

Binding Assay—The assay buffer was prepared by adding 12 g Hepes, 1.2 g $MgSO_4$ and 1.2 g BSA to 1000 ml of glass distilled water. A pH of 7.65 was obtained using 1N NaOH. The stock standard solution was made using assay buffer and was used for one week. The assay was performed in 12×75 mm glass test tubes by the addition of 100 μl of standard solution, 25 μl of receptor protein (150-200 μg/ml), 25 μl $^{125}$I-TP (80,000 cpm)) 20 μl of 1 percent Triton X-100, and the volume was made up to 200 μl with assay buffer. After incubation for 18 h at 4° C., 200 μl of human IgG (1.5 mg/ml) (as carrier) and 200 μl of 35 percent PEG-8000 in PBS, pH 7.56, were added, mixed, and incubated for 30 min on ice. The tubes were centrifuged and the residue was washed with 10 percent PEG in PBS, pH 7.3, and counted in an LKB-gamma counter.

The radioactivity in the precipitate in the presence of 1 mg/ml nonradioactive thymopoietin was taken to represent nonspecific binding. TCA was added to the supernatant (final concentration 5 percent) and precipitable radioactivity was measured. At all times this exceeded 95 percent, indicating minimal release of free $^{125}$I from the tracer.

Competition Experiments—Following the above binding assay procedure, $2.3\times10^{-10}$M of $^{125}$I-TP was incubated with 4 μg of receptor protein and test peptide together with the same concentration of the thymopoietin 37-45 nonapeptide. (H-VAL-GLU-LEU-TYR-LEU-GLN-SER-LEU-TNR-OH). The incubation was continued for 12 h, after which free and bound $^{125}$I-TP were determined as above. The nonapeptide is used to block an adjacent receptor site on the receptor protein. If this adjacent receptor site is not blocked, some labeled TP can bind to the receptor protein through this site even if the thymopentin receptor site is blocked by the test peptide. Such binding is unrelated to the activity of the test peptide and (if not blocked by the TP 37-45 nonapeptide) would yield inaccurate results.

The following representative compounds of the invention caused displacement at least 50% of that caused by thymopoietin self-displacement at equivalent concentrations:

H-ARG-LYS-ASP-VAL-PHE-OH;
N-α-acetyl-ARG-PRO-ASP-VAL-PHE-OH;
N-α-formyl-ARG-PRO-ASP-VAL-PHE-OH;
N-ARG-PRO-ASP-VAL-PHE-OH;
H-ARG-LYS-ASP-VAL-HIS-OH;
H-ARG-LYS-ASP-VAL-TRP-OH; and
H-ARG-LYS-ASP-VAL-TRP-$NH_2$ For comparison, other peptides such as insulin, glucagon, growth hormone, somatostatin, β-endorphin, FTS, ACTH, CRF, and ubiquitin caused no detectable displacement.

The above Examples have been presented for illustrative purposes only and not to limit the scope of the present invention, which scope is set out in the following claims.

What is claimed is:

1. A peptide having the formula:

R-V-W-X-Y-Z-$R^1$ or a pharmaceutically-acceptable acid- or base-addition salt thereof, wherein:

R is H, loweralkyl, formyl, or loweralkanoyl;
V is ARG or D-ARG;
W is [LYS, D-LYS,] PRO, dehydro-PRO, or AIB;
X is ASP, D-ASP, GLU, or D-GLU;
Y is VAL, LYS, LEU, ILE, GLU, ALA, GLN, D-VAL, D-LYS, D-LEU, D-ILE, D-GLU, D-ALA, or D-GLN;
Z is PHE, HIS, TRP, D-PHE, D-HIS, or D-TRP; *and*
$R^1$ is OH or $NR^2R^3$; and $R^2$ and $R^3$ are each independently selected from H or loweralkyl[; provided that when W is LYS, X is D-ASP, GLU, or D-GLU, and Y is VAL, Z is other than PHE].

2. The peptide of claim 1 wherein Z is PHE, HIS, D-PHE, or D-HIS.

3. The peptide of claim 2 wherein W is PRO.

4. The peptide of claim 1 wherein R is hydrogen or loweralkyl, V is ARG, X is ASP, and Z is PHE or HIS.

5. The peptide of claim 4 wherein W is PRO.

6. A peptide having the formula α-acetyl-ARG-PRO-ASP-VAL-PHE-OH or a pharmaceutically-acceptable acid- or base-addition salt thereof.

7. A peptide having the formula α-formyl-ARG-PRO-ASP-VAL-PHE-OH or a pharmaceutically-acceptable acid- or base-addition salt thereof.

8. A peptide having the formula α-(loweralkanoyl)-ARG-PRO-ASP-VAL-PHE-OH or a pharmaceutically-acceptable acid- or base-addition salt thereof.

9. A peptide having the formula H-ARG-PRO-ASP-VAL-PHE-OH or a pharmaceutically-acceptable acid- or base-addition salt thereof.

10. A peptide having the formula H-ARG-PRO-ASP-VAL-HIS-OH or a pharmaceutically-acceptable acid- or base-addition salt thereof.

11. A peptide having the formula H-ARG-LYS-ASP-VAL-HIS-OH or a pharmaceutically-acceptable acid- or base-addition salt thereof.

12. A peptide having the formula H-ARG-LYS-ASP-VAL-PHE-OH or a pharmaceutically-acceptable acid- or base-addition salt thereof.

13. A pharmaceutical composition comprising an effective T cell inducing amount of a peptide of claim 1 in admixture with a pharmaceutically acceptable carrier.

14. A pharmaceutical composition comprising an effective B cell inducing amount of a peptide of claim 1 in admixture with a pharmaceutically acceptable carrier.

* * * * *